United States Patent [19]

Sinclair et al.

[11] Patent Number: 5,086,058
[45] Date of Patent: Feb. 4, 1992

[54] METHOD FOR TREATING ALCOHOLISM WITH NALMEFENE

[75] Inventors: John D. Sinclair, Espoo; Harry Scheinin, Piispanristi; Risto Lammintausta, Turku, all of Finland

[73] Assignees: Alko Ltd., Helsinki; Orion-Yhtyma Oy, Espoo, both of Finland

[21] Appl. No.: 532,424

[22] Filed: Jun. 4, 1990

[51] Int. Cl.$^5$ ............................................. A61K 31/44
[52] U.S. Cl. ...................................... 514/282; 514/811
[58] Field of Search .................................. 514/282, 811

[56] References Cited

U.S. PATENT DOCUMENTS

| | | | |
|---|---|---|---|
| 4,857,533 | 8/1989 | Sherman et al. | 514/282 |
| 4,863,928 | 9/1989 | Atkinson et al. | 514/282 |
| 4,882,335 | 11/1989 | Sinclair | 514/282 |

Primary Examiner—Frederick E. Waddell
Assistant Examiner—Diane Gardner
Attorney, Agent, or Firm—Armstrong, Nikaido, Marmelstein, Kubovcik & Murray

[57] ABSTRACT

A method for treating alcoholism. The alcohol-drinking response of alcoholics is extinguished by having them drink alcoholic beverages while nalmefene, an opiate antagonist, blocks the positive reinforcement effect of ethanol in the brain.

4 Claims, 1 Drawing Sheet

METHOD FOR TREATING ALCOHOLISM WITH NALMEFENE

FIELD OF THE INVENTION

The present invention relates to a treatment for alcohol abuse in which the alcohol-drinking response is extinguished over a limited number of sessions by being emitted while reinforcement from alcohol is blocked with nalmefene.

BACKGROUND OF THE INVENTION

U.S. Pat. No. 4,882,335 discloses a method for treating alcoholism in which the learned response of alcohol drinking is extinguished by being emitted while the reinforcement from alcohol in the brain is blocked with an opiate antagonist.

The antagonists disclosed for use in the method described in U.S. Pat. No. 4,882,335, however, have various disadvantages. Of the antagonists specifically disclosed, i.e., naloxone, naltrexone, cycloazocine, diprenorphine, etazocine, levalorphan, metazocine, nalorphine and salts thereof, only naloxone and naltrexone are approved for general use. Naloxone cannot be taken orally. Naltrexone can be taken orally but because of a high first-pass metabolism, its oral availability is only 5%. Variability in first-pass metabolism also makes oral dosing with naltrexone less predictable than desired.

Naltrexone is also now considered to be a first-class hepatotoxin. Since alcohol abuse is frequently accompanied by liver damage, the use of naltrexone is counterindicated in patients with alcoholic liver cirrhosis and is questionable in other alcoholics that have not yet developed cirrhosis.

It is an object of the present invention, therefore, to provide a method for treating alcoholism in which the learned response of alcohol drinking is extinguished while the reinforcement from alcohol in the brain is blocked with an opiate antagonist which avoids the disadvantages of the antagonists previously disclosed for such use.

This and other objects and advantages of the present invention are accomplished with the use of the opiate antagonist nalmefene as described hereinafter.

SUMMARY OF THE INVENTION

According to the present invention there is provided a therapeutic method for extinguishing the alcohol-drinking response of alcoholics using the opiate antagonist nalmefene. The method consists of numerous sessions in which the alcoholic takes nalmefene and then drinks alcohol while sufficient amounts of nalmefene are present to block reinforcement from the alcohol.

DESCRIPTION OF THE PREFERRED EMBODIMENTS

Figure 1:
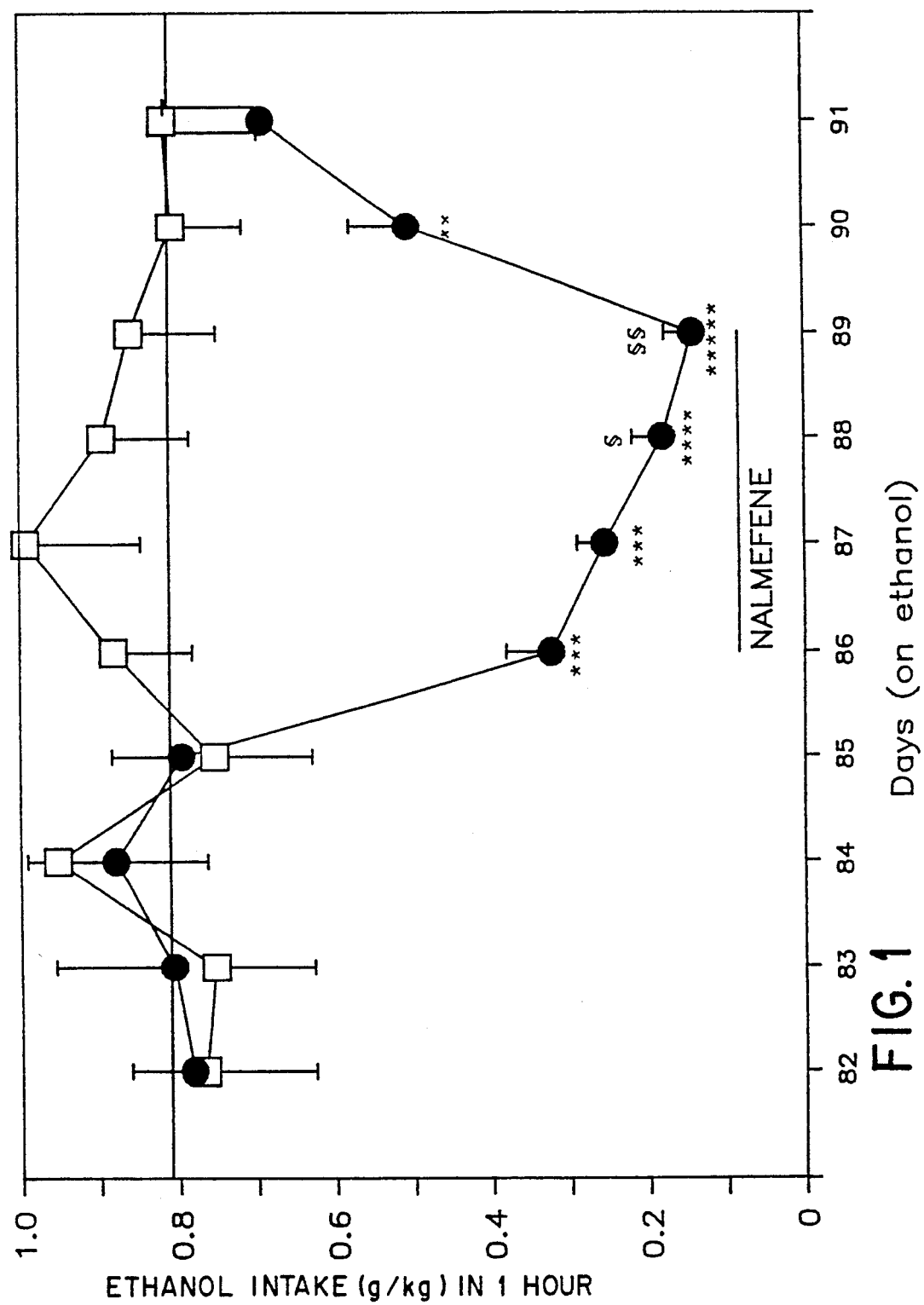
FIG. 1 shows the apparent extinction of alcohol drinking in AA rats caused by four daily 1 hour sessions of drinking alcohol after administration of nalmefene (mean ± standard error).

Individuals classified as being alcoholics or alcohol abusers are screened for counterindications such as Korsakoff's syndrome. Nalmefene is then given. It can be given by injection, transdermal administration, nasal administration, suppository, sublingual administration, and the like, but oral administration is preferred. Previous studies indicate that oral doses of up to 300 mg can be taken without clinically relevant side-effects (Dixon et al., *Clin Pharmacol* 27: 233–239, 1987). Yeomans et al. (*Psychopharmacology* 100: 426–432, 1990), however, reported that subjects were able to distinguish nalmefene from placebo with doses of 5 mg or more, but not with 2.5 mg. Since extraneous factors that distinguish the extinction session from normal drinking are likely to reduce the effectiveness of extinction, an initial dose of approximately 2.5 mg for patients weighing about 70 kg is preferred. The nalmefene can be taken in capsule form, but the procedure used by Yeomans et al. (1990) of giving it in grapefruit juice, or some other non-alcoholic beverage with a slightly bitter taste, will be less obtrusive.

Nalmefene can be used either in a program of non-selective or selective extinction of the alcohol-drinking response. In the non-selective program, nalmefene is given twice daily and the patients allowed to drink normally without supervision. Because active amounts of nalmefene are continually present during the treatment period, all alcohol drinking occurs in the absence of reinforcement. Extinction treatment with nalmefene administration is continued until the patient's alcohol intake is reduced to a level at which withdrawal symptoms begin. Nalmefene administration is then stopped and the patient treated in the normal manner for withdrawal.

In a program of selective extinction of the alcohol-drinking response, typically nalmefene is given about an hour before the beginning of an evening extinction session. During the session, the patient then drinks alcohol under supervision in a manner similar to his or her normal drinking practices as determined by an earlier interview given to the patient and/or associates. After the 4–6 hour session, abstinence is strictly enforced until the next nalmefene administration the following evening, e.g., by keeping the patient in the treatment center at all times except during the extinction sessions. Extinction sessions could occasionally be held in the daytime, especially for patients who previously had used alcohol frequently during the day or, early in treatment, for patients saying that they are experiencing severe craving or beginning withdrawal symptoms.

Non-selective extinction has the advantage of being easier to administrate and perhaps also of having the alcohol drinking occurring under more natural circumstances. Selective extinction on the other hand has the advantage that only the alcohol drinking response shows a net weakening over several days of treatment. Other responses, such as the eating of highly palatable food, which also are reinforced through the opiate system, might be weakened somewhat during one extinction session if they happen to be emitted while high levels of nalmefene are present. These responses, however, will regain their strength when they are emitted in the absence of nalmefene the next day and are thus again reinforced. The alcohol-drinking response, which can only be made while the reinforcement is blocked, becomes progressively weaker with each extinction session. Since the propensity to drink alcohol is a function of the relative strength of alcohol drinking in comparison to all competing responses, selective extinction will be more effective if competing responses are reinforced through the opiate system. Furthermore, it will preclude side-effects from weakening of other responses.

Extinction of the alcohol drinking response, either selectively or non-selectively, should not be expected to be successful alone in the treatment of alcoholism because the patient can readily relearn the response if drinking is attempted after the termination of nalmefene administration. However, once the extinction has been completed, the accompanying craving for alcohol should also be greatly reduced. Consequently, conventional methods for increasing the motivation and incentive for remaining abstinent should be sufficient to prevent relapse.

The duration of extinction treatment required for each patient will depend upon the severity of his or her alcoholism and the number of specific drinking situations in which the alcohol-drinking response must be extinguished. The duration of the extinction program can, therefore, range from about 1 to 5 weeks.

Once the alcohol-drinking response has been sufficiently weakened, the final extinction sessions can be conducted with an element of punishment. Although punishment is ineffective if positive reinforcement is still being produced by the same response, punishment may be useful while the positive reinforcement is blocked. Examples of punishment include mild electric shock when alcohol is consumed, production of conditioned taste aversions from very large doses of alcohol with or without emetics, aversion therapy with an alcohol-sensitizing compound such as disulfiram or cyanamide, and the like.

After the final extinction session, the patient is told to abstain from all alcohol in the future. Various procedures can be used to help ensure that the patient does in fact refrain from drinking alcohol. Such procedures include counseling, psychotherapy, family therapy, job therapy, joining Alcoholics Anonymous, and the like. Efforts should also be taken to help the patient resume a normal productive life and avoid situations and other stimuli previously associated with alcohol drinking.

The patient can also be informed that although his or her alcohol-drinking response has been extinguished in the most frequently used drinking situations, it is possible that some have been missed. Consequently, if the patient anticipates or is experiencing a situation in which the response has not yet been extinguished, he or she should request additional extinction sessions with nalmefene involving this new situation. This can be combined with a program of cue exposure, in which the patient is instructed first to take nalmefene and then to engage in all of the activities normally involved in alcohol drinking but refrain from actually drinking alcohol. If the patient succeeds in not drinking, the repeated exposure to the cues should reduce their ability to trigger alcohol drinking, but if the patient occasionally fails to abstain, the drinking in the presence of nalmefene will constitute an additional extinction session, further weakening the alcohol-drinking response. Alternatively, the patient can be kept on a maintenance program with continued administration of nalmefene.

The method according to the present invention for extinguishing alcohol drinking using nalmefene avoids the disadvantages associated with the use of naloxone and naltrexone and provides various advantages.

Nalmefene can be taken orally and has a 40-50% oral availability. Additionally, first-pass metabolism does not vary significantly with nalmefene. Oral administration of nalmefene offers the usual advantages (e.g., patient acceptability) and also an important advantage over injection specific to the extinction procedure. Namely, injection itself may act as a clear stimulus distinguishing the treatment sessions from normal drinking and thus lessening the effectiveness o extinction.

Extensive research has indicated that nalmefene is safe for human use and there is currently no evidence of side-effects or adverse reactions that would limit its use with alcoholics.

The elimination half-life of nalmefene, about 8 hours in humans, is suitable for selective or non-selective extinction of alcohol drinking a described hereinbefore.

Nalmefene is much more potent than naloxone —28 times more potent in precipitating withdrawal from opiate dependence in the rat as measured by a sudden rise in tail skin temperature (Katovich et al. *Substances and Alcohol Actions/Misuse* 5: 87-95, 1984)—and also somewhat more potent than naltrexone. Nalmefene is highly specific opiate antagonist without intrinsic agonistic activity, and thus with no abuse potential of its own. Subjective effects of the antagonist are minimal: e.g., a recent study on feeding (Yeomans et al., *Psychopharmacology* 100: 426-432, 1990) reported only a slight increase in self-rated alertness and decreases in ratings of both tiredness and elation.

The present invention is further illustrated by the following example which shows that nalmefene is very effective in suppressing alcohol drinking in rats, apparently through the extinction of their alcohol-drinking response and that nalmefene administered orally is also effective.

EXAMPLE

Extinction of alcohol drinking with nalmefene

Methods

Male rats from the $F_{56}$ generation of the AA line were used. The AA rat line has been developed in the laboratory of Alko Ltd., the Finnish State Alcohol Company, by selective breeding for high alcohol consumption. It is believed to be a suitable animal model for studying the effect of pharmacological treatments on alcohol drinking, and especially heavy alcohol drinking induced partially by a genetic predisposition.

Thirty rats were given a choice between 10% (v/v) ethanol solution and water in graduated 100 ml Richter tubes. Alcohol was continually available during the first 36 days, but thereafter for only 1 hour each day (15:30 to 16:30). Standard rat food was always available; food jars were weighed daily approximately 20 min. before alcohol access began. Nalmefene treatment began after 85 days on alcohol (when the mean ($\pm$SE) body weight was 399$\pm$9 g), with the alcohol consumption (as g of absolute ethanol per kg body weight) during the last 4 days forming the baseline for dividing the animals into two matched groups. One group was injected subcutaneously with 0.36 mg/kg of nalmefene (as a 0.18 mg/ml solution in normal saline) and the other group with an equivalent volume of saline on each of the next 4 days, 20 min. before access was given to alcohol.

Results

Administering nalmefene before providing access to alcohol progressively decreased alcohol drinking (FIG. 1). The alcohol intake was significantly lower on each treatment day than the animals' own baseline (* $p<0.0001$,  $p<0.00001$, *** $p<0.000001$) and also significantly lower than the alcohol intakes on corresponding days by the saline-injected controls (□ in FIG. 1). The alcohol intakes after the third and fourth nalmefene injections were both significantly lower than that after the first injection, i.e., on Day 86 (§ p=0.022, §§ p=0.002), illustrating the progressing decrease. This cannot be explained as a direct effect of nalmefene. The half-life of nalmefene in rats is about one hour and there is no accumulation or sequestering in specific tissues. Consequently, essentially all nalmefene from one injection would have been eliminated after 24 hours when the next injection was given, and the systemic levels should have been the same on each of the 4 treatment days. The progressive decrease, however, resembles the results in extinction studies, and is what would be expected if the alcohol-drinking response got weaker each day when it was emitted while reinforcement was blocked.

One day after the last nalmefene injection, the alcohol intake was still significantly lower than baseline (** p=0.0002) and significantly lower than that by the controls (p=0.014). Since there should have been no nalmefene left in the rats' systems at this time, the decrease cannot be attributed to a direct action of the antagonist. It is, however, consistent with the hypothesis that the alcohol-drinking response had been progressively extinguished on the 4 preceding treatment days Previous operant conditioning studies have shown that alcohol is more reinforcing for AA rats than for rats of unselected strains, and that the AA rats learn alcohol-reinforced responses more rapidly. Consistent with these findings, the present AA animals rapidly relearned the alcohol-drinking response and their alcohol drinking was no longer significantly reduced on the second day after the termination of nalmefene treatment.

There were no significant differences on any day between the nalmefene and control groups in water drinking, food intake, or body weight changes, nor any other indication of detrimental effects from nalmefene.

Oral nalmefene

Subsequently, all the rats were returned to continual access to ethanol. After their intake had stabilized, on the 115th day on alcohol, nalmefene was added to the food of the rats that had been the saline-injected controls in the first part of the study. The amount of nalmefene was calculated on the basis of prior food intake to produce a daily intake of 18 mg/kg body wt (i.e., 404 mg/kg food), an oral dose roughly equivalent to the 0.36 mg/kg dose given by injection.

Oral nalmefene also reduced alcohol drinking. The alcohol intake by each of the 15 rats on nalmefene decreased, with the mean ($\pm$SE) going from $6.51\pm0.25$ g/kg during the preceding week to $4.80\pm0.34$ on the first nalmefene day (t=8.86, 14 df, p=0.0000004 relative to their own baseline; t=6.52, 28 df, p=0.0000005 relative to the 15 animals without nalmefene whose alcohol intake remained relatively constant: $6.31\pm0.22$ vs. $6.15\pm0.28$ g/kg).

The alcohol intake for the entire 4 days when nalmefene was in the food was significantly reduced (t=12.81, 14 df, p=0.000000004 relative to baseline; t=4.79, 28 df, p=0.00005 relative to controls). At noon on the next day, i.e., 6 h after food intake during the active dark period should have stopped, and 6 h before it would be expected to be resumed, normal food without nalmefene was returned. During the following night, although essentially no nalmefene should have been in their systems, their alcohol drinking remained significantly suppressed ($4.96\pm0.33$ g/kg; t=7.9 14 df, p=0.000002, relative to baseline; t=3.55, 28 df, p=0.001, relative to controls). Subsequently, alcohol drinking returned to the pre-nalmefene baseline.

These results indicate that nalmefene is effective in suppressing alcohol drinking in rats, not only when injected, but also when administered by the preferred oral route.

We claim:

1. A method for treating alcoholism by extinguishing the alcohol-drinking response, comprising the steps of:
   repeatedly administering nalmefene to a subject suffering from alcoholism;
   while the amount of nalmefene in the subject's body is sufficient to block the stimulatory effect of alcohol, having the subject drink an alcoholic beverage; and
   continuing the steps of administering nalmefene and drinking an alcoholic beverage until the alcohol-drinking response is extinguished.

2. The method of claim 1 further comprising the step of punishing the patient after the alcoholic beverage is consumed, said step of punishment being selected from the group consisting of administration of electric shock, administration of emetics, and administration of an alcohol sensitizing compound.

3. The method of claim 1 further comprising continuing the administration of nalmefene after the alcohol-drinking response is extinguished.

4. The method in accordance with claim 1 wherein the dose of nalmefene is from 0.1 to 300 mg daily.

* * * * *